US00PP14668P39

(12) United States Plant Patent
Rushing

(10) Patent No.: US PP14,668 P3
(45) Date of Patent: Apr. 6, 2004

(54) *NANDINA DOMESTIC* PLANT NAMED 'JAYTEE'

(50) Latin Name: *Nandina domestica*
Varietal Denomination: Jaytee

(76) Inventor: Ralph C. Rushing, 3220 Redstone Dr. West, Semmes, AL (US) 36575

( * ) Notice: Subject to any disclaimer, the term of this patent is extended or adjusted under 35 U.S.C. 154(b) by 240 days.

(21) Appl. No.: 09/893,950

(22) Filed: Jun. 29, 2001

(65) Prior Publication Data

US 2003/0019001 P1 Jan. 23, 2003

(51) Int. Cl.[7] ..... A01H 5/00
(52) U.S. Cl. ..... Plt./235

(58) Field of Search ..... Plt./235

(56) References Cited

U.S. PATENT DOCUMENTS

PP5,560 P * 9/1985 Rushing ..... Plt./54

* cited by examiner

*Primary Examiner*—Anne Marie Grunberg

(57) ABSTRACT

'Jaytee', a new and distinct variety of *Nandina domestica*, which exhibits characteristics of form, size, vigor, leaf coloration, and fruiting not known to exist in other varieties of *Nandina domestica*. These characteristics include vigorous, aggressive growth, abundant fruit and flowers, and unique leaf coloration. This plant has a rhizomatous growth habit that results in a compact, dense plant with no tendency to legginess.

5 Drawing Sheets

Latin name of the genus and species: *Nandina domestica*. Variety denomination: 'Jaytee'.

CROSS REFERENCE TO RELATED APPLICATIONS

*Nandina domestica* Thunb. called 'Lowboy', U.S. Plant Pat. No. 5,560.

STATEMENT AS TO RIGHTS TO INVENTIONS MADE UNDER FEDERALLY-SPONSORED RESEARCH AND DEVELOPMENT

None.

BACKGROUND OF THE INVENTION

1. Field of Invention

The present Invention relates to a new and distinct cultivar of Nandina plant, botanically known as *Nandina domestica* and hereinafter referred to by the cultivar name 'Jaytee'. This new Nandina is a product of a seedling selection program conducted by the inventor at Rushing Nursery, Inc., Semmes, Ala.

2. Description of Relevant Prior Art Including Information Disclosed Under 37 CFR 1.56.

The new Nandina originated as a chance seedling of *Nandina domestica*, originating from seed collected from a bed of Nandina containing one named and many unnamed varieties. The named variety is *Nandina domestica* 'Harbour Dwarf' (unpatented). 'Jaytee' fruits more abundantly, has a denser more rhizomatous and vigorous habit, and exhibits a broader color spectrum of leaf color and heavier textured leaves than 'Harbour Dwarf'. 'Jaytee' is lower growing, more rhizomatous, and exhibits leaves of heavier texture with a broader color spectrum than 'Lowboy'. Stem cutting propagation of 'Jaytee' has been performed by the inventor at Rushing Nursery, Inc., Semmes, Ala. Tissue culture propagation has been accomplished at Magnolia Gardens Nursery, Waller, Tex. Both methods have shown that the unique features of this new Nandina are stable and reproduced true to type in successive generations.

SUMMARY OF THE INVENTION

The 'Jaytee' cultivar has been observed and extensively tested in different growing situations for five years. Its recognizable characteristics, which distinguish it from other known Nandina cultivars are:

1. Compact, dense form, spreading by rhizomes, with a mature height of 18–22".
2. Aggressive, vigorous growth.
3. Has proven adaptable to harsh environmental conditions.
4. Abundant flowers and fruit at an age of 1½ years.
5. Exhibits unique leaf coloration.

New growth is dark, reddish brown.

Intermediate growth is light green with reddish hues.

Mature winter foliage is purple with pinkish hues and dark green with yellow tint.

Leaves are large and appear thick and heavily textured.
6. Is sun and shade tolerant maintaining its proportions equally well in both conditions.
7. Versatile uses are: groundcover, mass plantings, and individual specimens.
8. Has shown no susceptibility to mosaic virus.
9. Has survived –6 degrees in Zone 6. Winter hardiness testing is being continued.
10. Has proved to be adaptable to extreme landscape conditions, where 'Harbour Dwarf' would have difficulty in becoming established.

TABLE 1

Comparison: 'Jaytee' and 'Harbour Dwarf'

| | Applicant ('JayTee') | Harbour Dwarf (unpatented) |
|---|---|---|
| Height | 18–22" | 27–36" (taller in heavy shade) |
| Width | 30–36" | 24" |
| Leaf Length | 30–34 mm | 28–30 mm |
| Leaf Width | 18–20 mm | 16–18 mm |
| Leaflet Length | 5.5–7 mm | 5–6 mm |
| Leaflet Width | 2.5–3 mm | 1.5–2 mm |
| Foliage | Opposite, bipinnate, compound evergreen | Opposite, bi-tripinnate, compound evergreen |
| New Foliage Color | Dark, reddish brown (RHS 174A) | Light green with pinkish hues (RHS 143A) |
| Intermediate Foliage Color | Light green with reddish hues (RHS 140A) | Light yellowish-green (RHS 144A) |
| Mature Foliage Color | Dark green (RHS 136A) | Dark green (RHS 139A) |
| Winter Foliage Color | Purple with pinkish hues (RHS N187A) and Dark greenish with yellow tint (RHS 147A) | Orange to bronzy red to reddish purple (RHS 173) |
| Foliage Texture | leathery in appearance | somewhat leathery in appearance |
| Rachis Color | Reddish-purple (RHS 71A) | Brownish-orange (RHS 176B) |
| Flowers | Numerous perfect flowers that are white in bud, with yellow anthers, Flowers develop in May–June. | Occasionally flowers with perfect flowers that are slightly pink in bud, turning white with yellow antlers. |
| Fruit | Abundant clusters of red (RHS 43A) berries. Typically larger than those of 'Harbour Dwarf.' 8–9 mm diamter. | Few small red (RHS 42A) berries, sparingly produced. 6–7 mm diameter |
| Growth Habit | Dense, dwarf, compact mounding form. Aggressive, vigorous, spreading by rhizomes. Maintains fullness with no tendancy toward legginess. | Dwarf form, stiff wide-spreading crown, becoming more graceful in appearance with age. Tendency towards legginess in shade. |
| Disease | no mosaic virus susceptibility to date | Susceptible to mosaic virus |

TABLE 2

Comparison - 'Jaytee' and other Nandina cultivars

| | Mature Size | Other Characteristics |
|---|---|---|
| Jaytee | 18–22" × 30–36" | as previously described |
| Heavenly Bamboo | 6–8' H | perennating by rhizomes, prone to legginess, generally fruits abundantly |
| Compacta | 4–6' H | perennating by rhizomes, fruiting capability dependent on selection |
| Moonbay | 3–3½' H | not rhizomatous, flowering sparse to nil |
| Gulf Stream | 3–3½' H | not rhizomatous, flowering sparse to nil |
| Lowboy | Typically 2–3' H × 3.5' W. Will reach 5' H × 3.5' W in shade | typical species leaf coloration, moderately rhizomatous, good fruit set |

BRIEF DESCRIPTION OF THE DRAWINGS

FIG. 1-A is a color photograph of the original plant 'Jaytee' growing in a landscape setting. The original plant has never been pruned and is 18" in height at 6 years of age.

FIG. 1-B is a photograph of the new variety growing in a 20-gallon container. This photo shows how rhizomatous this plant is.

FIG. 2-A is a side-by-side comparison of the new variety, shown on the right, with a 'Harbour Dwarf' shown on the left. Both plants are in a 3-gallon container at approximately 16 months of age.

FIG. 2-B represents the same plants as FIG. 2-A, but as a top view. 'Jaytee' on the right and 'Harbour Dwarf' on the left.

FIG. 3-A is a side-by-side comparison of the new variety's leaf color progression. From left to right is new growth, intermediate growth (2), and mature growth.

FIG. 3-B is a photograph of the new variety in a landscape setting. This photo shows the plant's unique leaf color in the summer.

FIG. 4-A is a photograph of the new variety's fruit.

FIG. 4-B is a photograph of the new variety's leathery leaf texture. It also shows the reddish-brown new growth.

FIG. 5-A is a photograph showing the new variety's flower buds.

FIG. 5-B is a photograph of the new variety's mature winter color.

DETAILED BOTANICAL DESCRIPTION

In the following description, color references are made to The Royal Horticultural Society Colour Chart except where general terms of ordinary dictionary significance is used. The following observations and measurements describe plants grown in landscape settings in Mobile, Ala.

Botanical classification: *Nandina domestica* cultivar 'Jaytee'.

Parentage: A chance seedling in a population of *Nandina domestica.*

Plant description: Appearance: Dwarf, dense, compact mounding form. Aggressive and vigorous in growth with a rhizomatous spreading habit, and unique foliage coloration and texture.

Plant height: 18–22 inches.

Plant width: 30–36 inches.

Foliage description:

*Arrangement.*—Opposite, bipinnately compound, evergreen.

*Leaflet base.*—Obtuse.

*Leaflet tips.*—Acuminate.

*Leaflet shape.*—Ovate-Lanceolate.

*Leaflet margin.*—Entire.

*Leaflet length.*—5.5–7 mm.

*Leaflet width.*—2.5–3 mm.

*Length.*—30–34 mm.

*Leaf width.*—18–20 mm.

*Stem form.*—Upright.

*Stem texture.*—Smooth, longitudinally ridged.

*Leaflet texture.*—Leathery appearance.

*Leaflet color.*—Young leaflets: Closest to RHS 174A — dark brownish red. Intermediate leaflets: Closest to RHS 140B — very light green with reddish hues. Medium leaflets: Closest to RHS 139A — medium green. Mature leaflets: Closest to RHS 136A — dark green. Winter color: RHS-N187A — purple with pinkish hues and RHS 147A — dark greenish with yellow tint. Abaxial Leaf Surface: Young leaflets — Closest to RHS 182C — reddish brown Intermediate leaflets — Closest to RHS 139C — green with reddish hues. Mature leaflets — Closest to RHS 137B — green. Midvein: Young leaflets — Closest to RHS 63A — reddish purple. Intermediate leaflets — Closest to RHS 59C — dark reddish purple. Mature leaflets — Closest to RHS 137C — green.

Inflorescence description:

*Appearance.*—Delicately showy inflorescence borne on terminal erect stalked panicles, consisting of 100 to 150 individual perfect flowers. Inflorescence conical in shape. Individual flowers actinomorphic with 6 white petals. Closest to RHS 155B. Petals are obovate with acute apex.

Inflorescence bud: Length: 7–9 mm. Diameter: 4–5 mm. Closest to RHS 155C — white.

Inflorescence size:

*Panicle.*—Height: about 12 cm. Width: about 6.5 cm.

*Individual flower.*—Diameter about 1.5 cm.

*Petals.*—Length: 5 mm. Width: 3 mm.

Reproductive organs:

*Androecium.*—6 stamens. Length about 4 mm. Closest to RHS 13B — yellow. The filament is insignificant as to be not visible.

*Gynoecium.*—Pistil superior. Length about 4 mm. Width about 1.5 mm. Ovary: Color Closest to RHS 159D — white. Style: Color Closest to RHS 159D — white. Stigma: Small and not prominent. Closest to 39A — reddish orange.

Blooming duration: 10 to 14 days.

Bloom lastingness: 1 to 3 days.

Fragrance: Weak ammonia scent. Not significant.

Seed: Fruit is 1 to 2 seeded. Seeds are hemispherical and concave on one side. 5–6 mm wide, 3–4 mm thick. Closest to RHS 177A — brown.

Rhizome description: The rhizomes spread horizontally underground, producing roots at the nodes. New shoots may develop at the nodes and produce new plants complete with roots, stems, and leaves. Rhizome: 3–5 mm diameter, closest to RHS 200A. Internode length: 10–20 mm.

Climatic range: This plant has survived winter temperatures as low as −6 degrees F. in Shrewsbury, Pa. (Zone 6).

Disease resistance: Has shown no susceptibility to mosaic virus.

It is claimed:

1. A new and distinct cultivar of *Nandina domestica* plant named 'Jaytee', as illustrated and described.

Figure 1-A
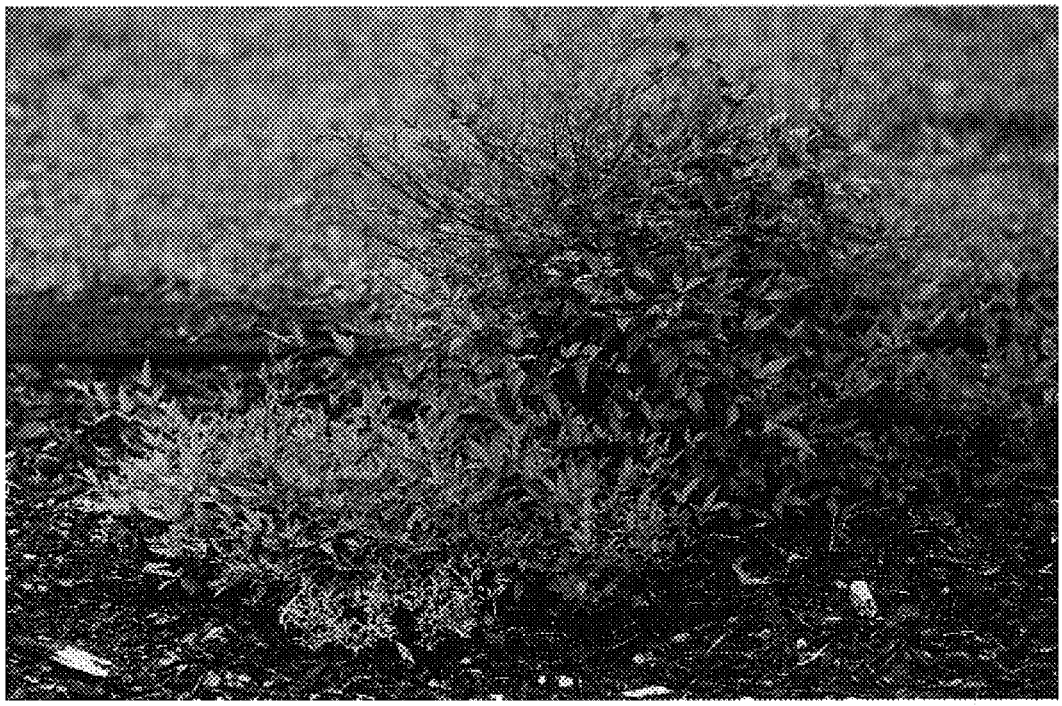
Figure 1-B
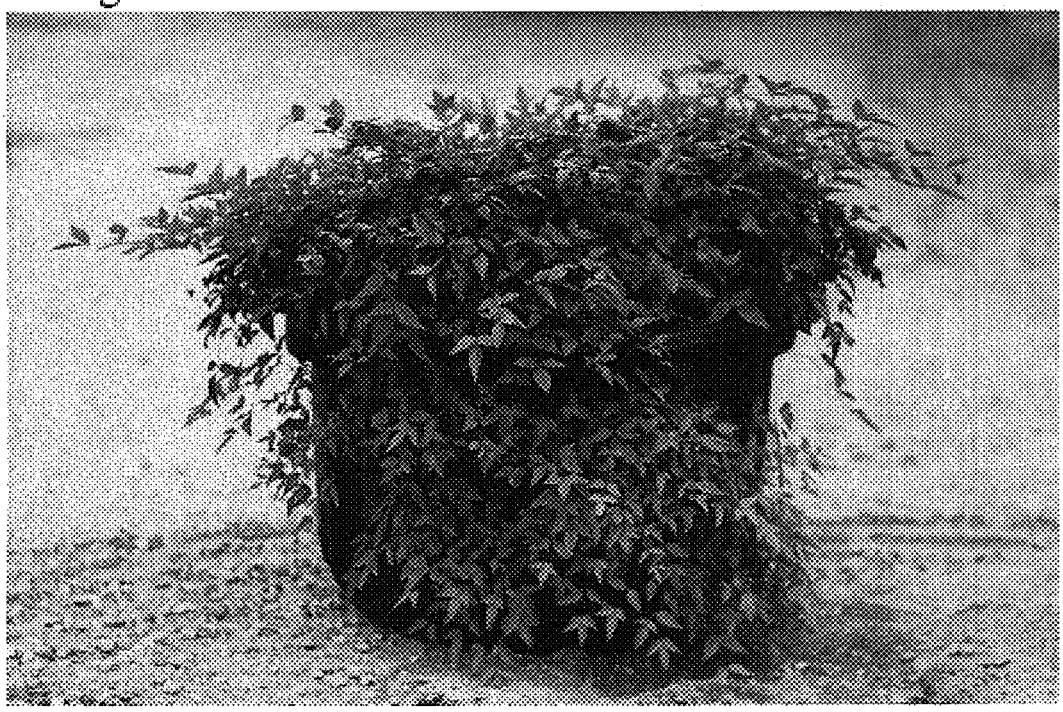

Figure 2-A
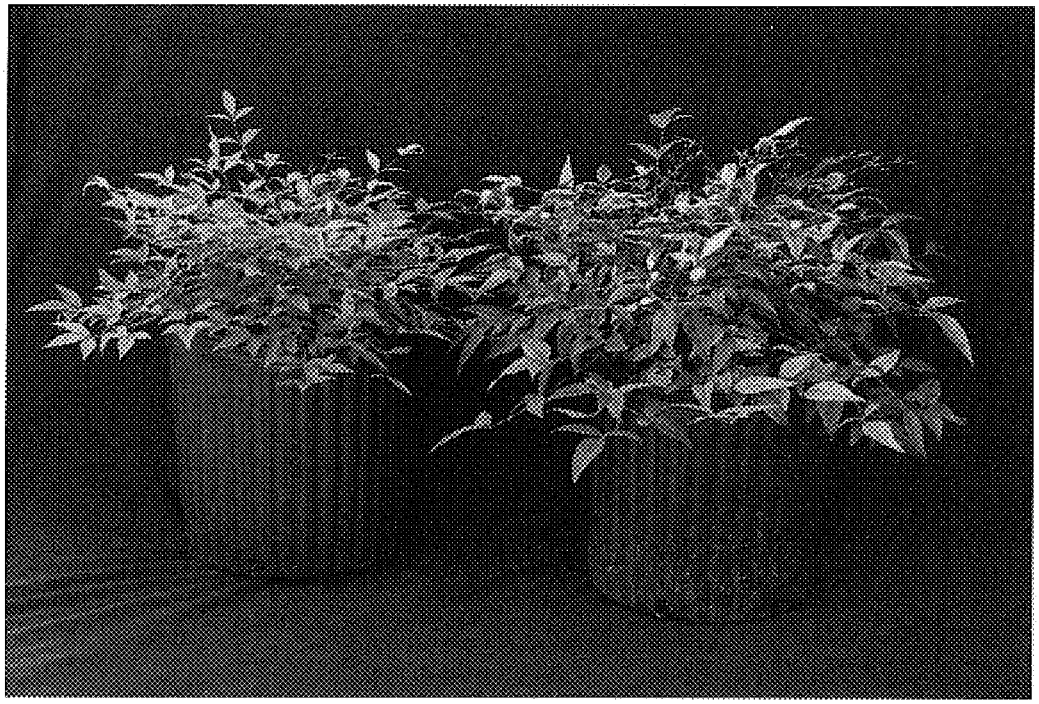
Figure 2-B
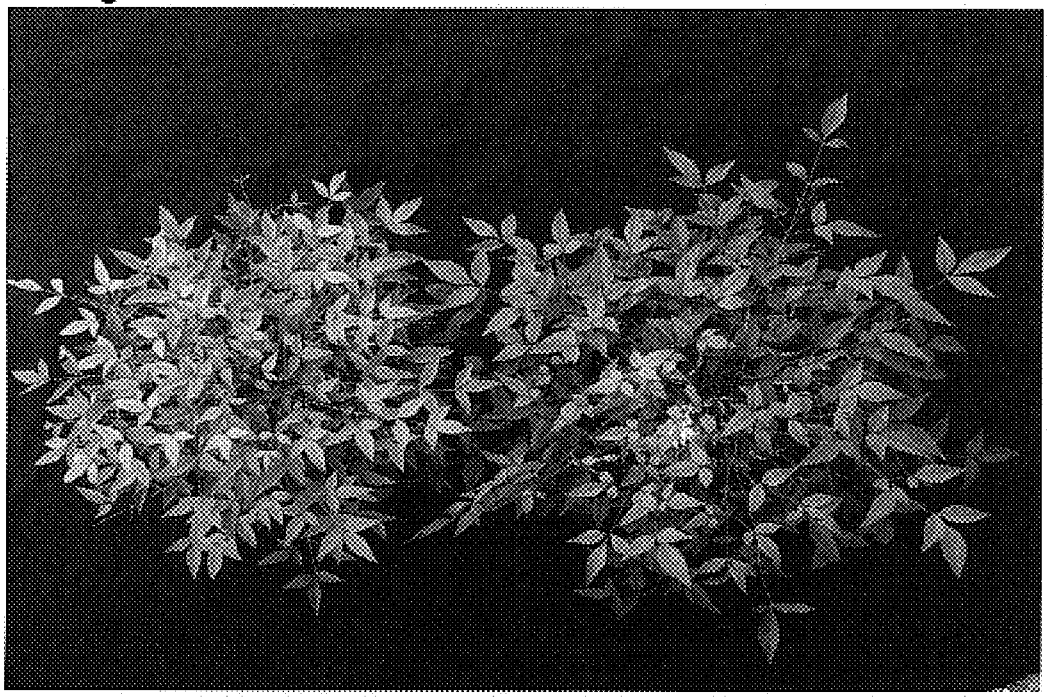

Figure 3-A
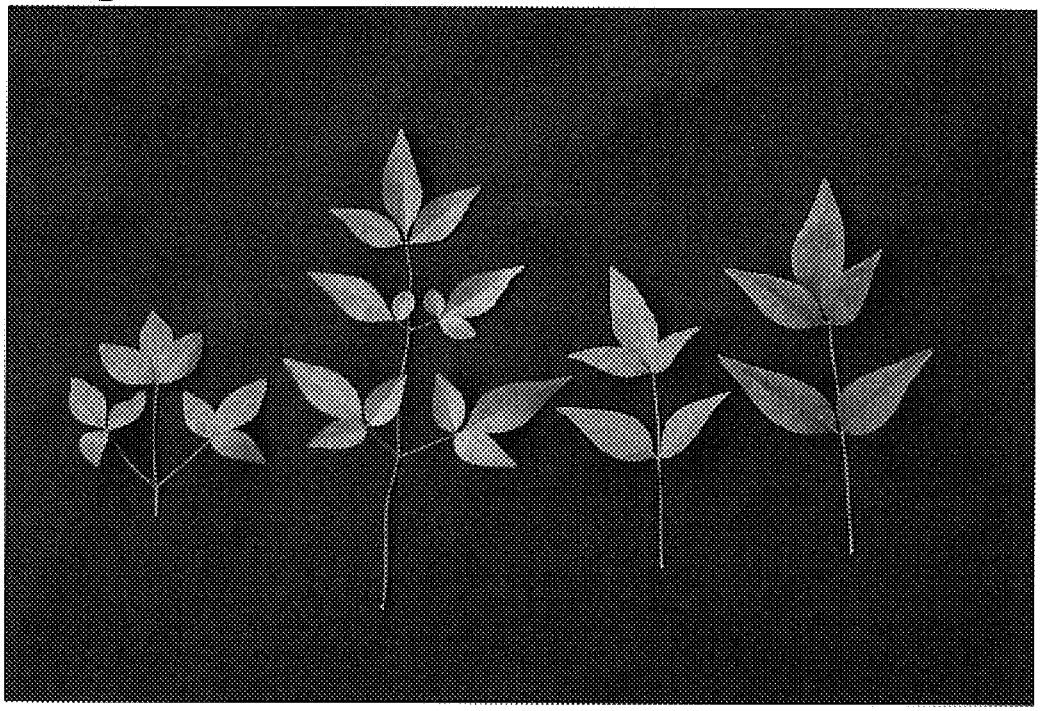
Figure 3-B
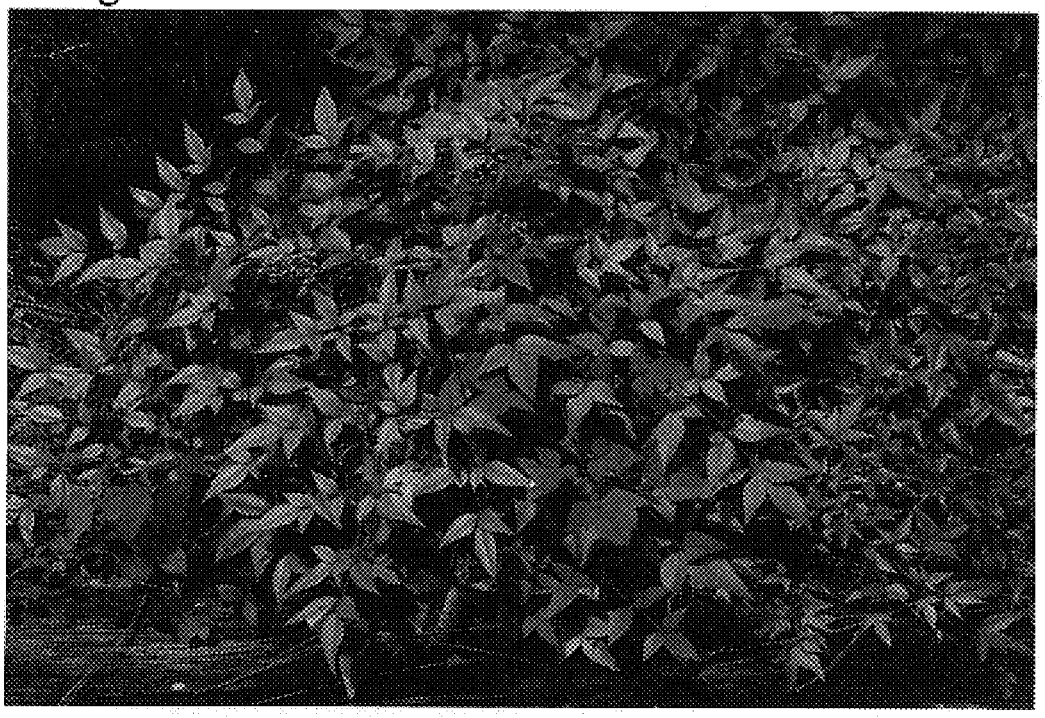

Figure 4-A
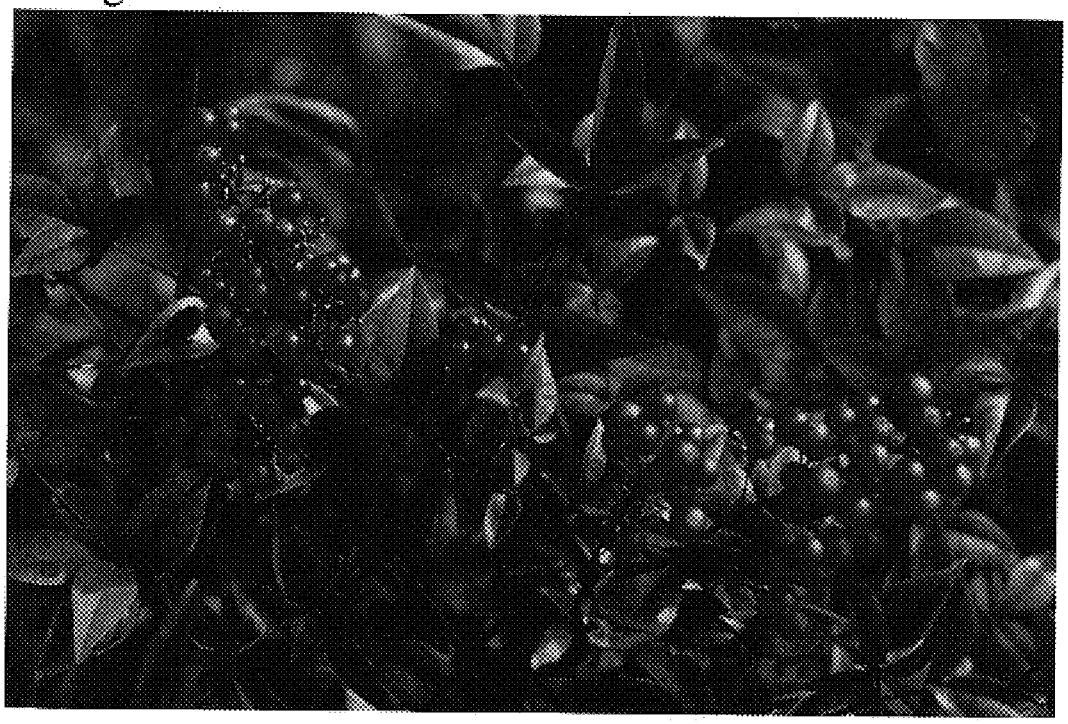
Figure 4-B
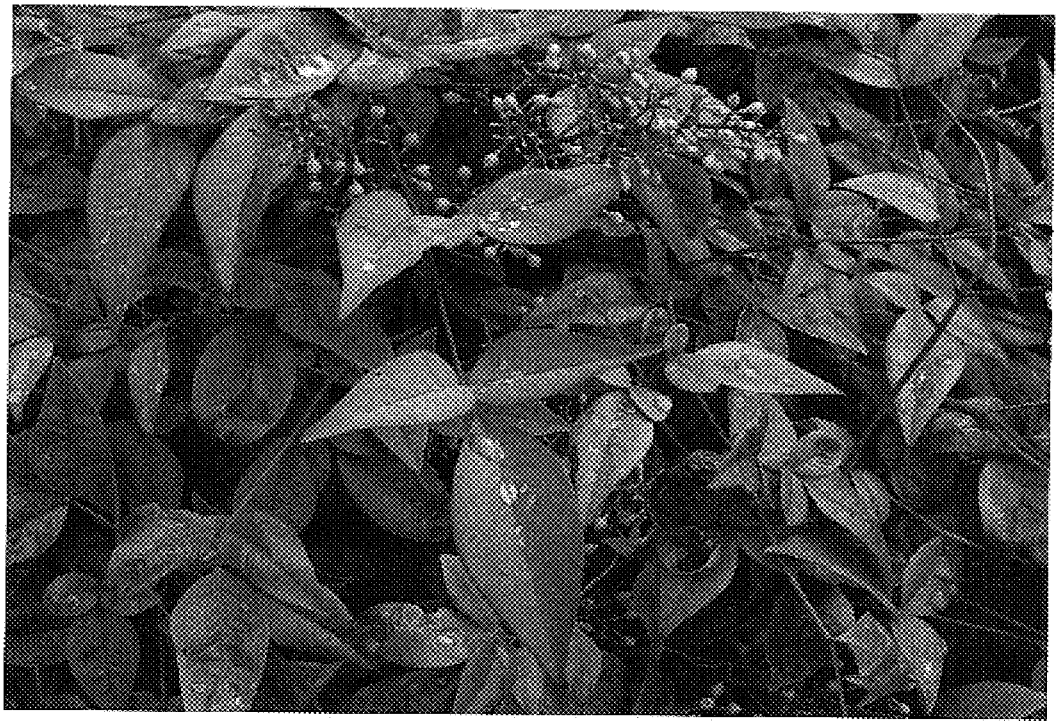

Figure 5-A
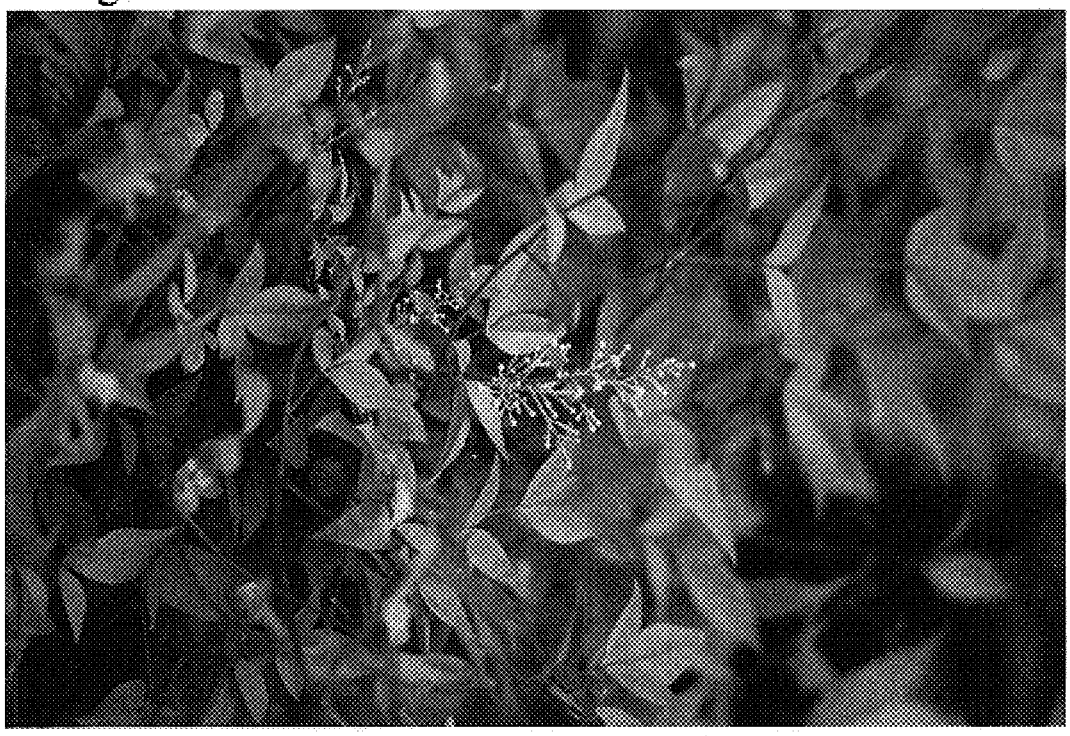
Figure 5-B
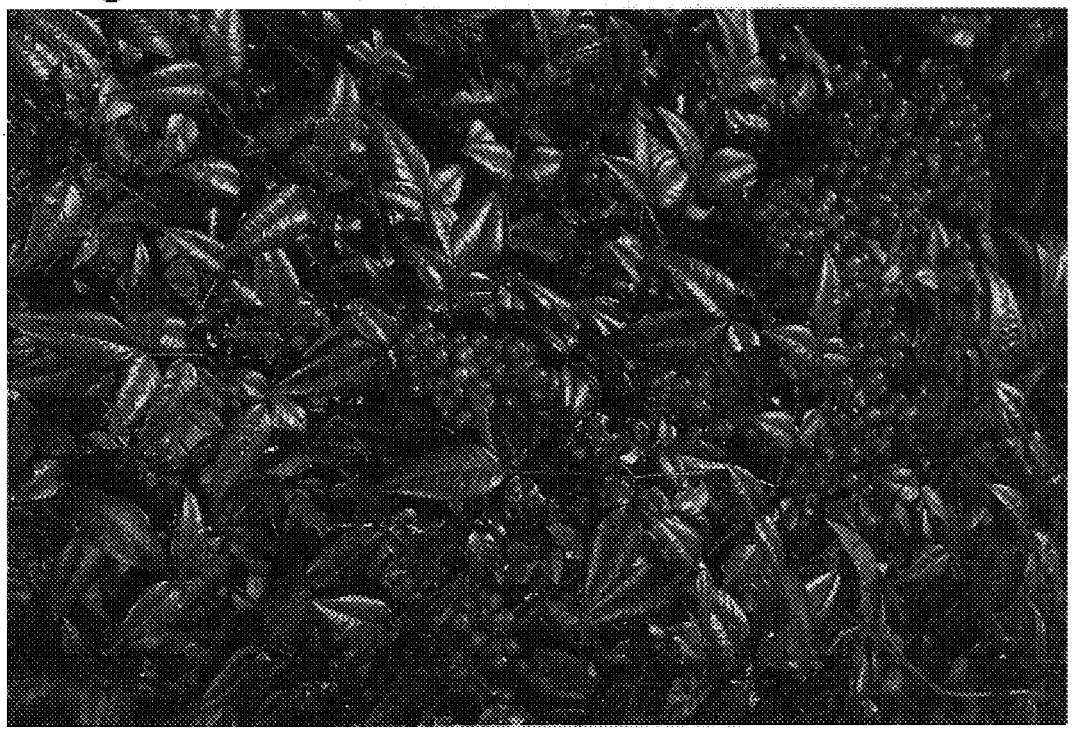

* * * * *